United States Patent [19]

Swanson

[11] Patent Number: 4,820,970

[45] Date of Patent: Apr. 11, 1989

[54] APPARATUS AND METHOD FOR USING MICROWAVE RADIATION TO MEASURE WATER CONTENT OF A FLUID

[76] Inventor: Claude V. Swanson, 1800 Old Meadow Rd., McLean, Va. 22101

[21] Appl. No.: 57,026

[22] Filed: Jun. 3, 1987

Related U.S. Application Data

[63] Continuation-in-part of Ser. No. 906,952, Sep. 15, 1986.

[51] Int. Cl.$^4$ .................... G01R 27/04; G01R 27/26
[52] U.S. Cl. ................... 324/58.5 A; 324/58 A; 324/58.5 R
[58] Field of Search .......... 324/58.5 A, 58 A, 58.5 R

[56] References Cited

U.S. PATENT DOCUMENTS

| | | | |
|---|---|---|---|
| 3,851,244 | 11/1974 | Mounce | 324/58.5 A |
| 4,135,131 | 1/1979 | Larson et al. | 324/58.5 A |
| 4,301,400 | 11/1981 | Paap | 324/58.5 A |
| 4,484,133 | 11/1984 | Riggin | 324/58.5 A |
| 4,634,963 | 1/1987 | Lunden | 324/58.5 A |

Primary Examiner—Reinhard J. Eisenzopf
Assistant Examiner—Anthony L. Miele
Attorney, Agent, or Firm—Marks Murase & White

[57] ABSTRACT

A microwave system for determining the volume fraction of water in a fluid. In the described application, the fluid is crude oil, and the system is used to determine the volume fraction of water in the crude oil. A microwave beam having a frequency which varies with time is transmitted through the liquid, and absorption losses are calculated. The volume fraction of water is determined according to the absorption losses.

17 Claims, 4 Drawing Sheets

APPARATUS AND METHOD FOR USING MICROWAVE RADIATION TO MEASURE WATER CONTENT OF A FLUID

BACKGROUND OF THE INVENTION

This is a continuation-in-part of application Ser. No. 906,952, filed Sept. 15, 1986.

The present invention relates to method and apparatus for using microwave radiation to measure the volume fraction and/or spatial distribution of a first fluid in a mixture of that fluid and a second fluid such as an oil-water mixture. It is especially useful for measuring water infiltration in a crude oil pipeline.

A multitude of devices are used to measure the water content of oil or other organic fluids, with special attention being paid to the measurement of the water content of crude oil. These devices find special utility when used as monitors on oil pipelines or oil loading pipes used for loading oil tankers. In general, they measure water content by measuring the attenuation due to absorption of a single microwave beam transmitted across a conduit carrying the oil. They are intended to detect and measure water which is dispersed in the oil in the form of a homogeneous distribution of fine droplets. For example, U.S. Pat. No. 4,301,400 to Hans J. Paap, U.S. Pat. No. 4,289,020 also to Hans J. Paap, and U.S. Pat. No. 3,498,112 to D. D. Howard disclose such devices. It is a known embellishment on these devices to use gamma radiation in conjunction with the single microwave beam in order to obtain a more accurate and reliable measurement of water content.

As mentioned, these devices are in general useful only for determining the volume fraction of water which is dispersed in oil as fine droplets, and not for detecting the presence of large "slugs" or globules or water which may be present in a pipeline. This is a disadvantage in systems where it is necessary to detect such large globules of water to prevent costly damage to equipment. For example, large slugs of water could devastate refinery equipment.

SUMMARY OF THE INVENTION

The present invention is preferably embodied in a device having a microwave generator which generates microwave beams in the frequency range between 1 and 200 GHz. The device then measures the attenuation of the beams as they propagate through the fluid. One embodiment of the device comprises first means, on one side of a volume of the fluid, for generating first and second microwave beams; second means, arranged across the volume from the first means, for receiving the first and second generated microwave beams after they have been attenuated at least in part by the water in the fluid and for generating at least one signal indicative of degree of attenuation of the first and second microwave beams; and third means, electrically connected to the second means and responsive to the at least one signal, for computing a volume fraction of water in the fluid based on the at least one signal. The two microwave beams differ from each other in at least one characteristic, such as frequency or path through the fluid, or both. The beams may also be differentiated by timing. This device can be generalized to include a plurality of microwave generators and corresponding microwave transmitters arranged in co-extensive linear arrays on either side of the volume.

In another embodiment, the water content of crude oil or other materials is measured by sweeping the microwave frequency quickly and continuously or in many small steps over a wide range of frequencies, from frequencies below 10 GHz to frequencies above 20 GHz. In microwave technology, this is known as "chirping" the signal. The attenuation across the beam volume is measured continuously as a function of frequency during the "chirp", and a mathematical process based on the Laplace inverse transform is used to analyze the attenuation and compute the water volume directly in the beam. A chirp would be done quickly, in less than one second, and possibly as fast as one millisecond. The cycle would be repeated continuously.

Here and throughout the specification and claims, the term "mixture" will be applied to any sharing of a given volume by two fluids which maintain their respective physical and chemical identities. Thus, the term is intended to encompass terms such as "suspension" or "sol". It is also intended to cover circumstances wherein a substantially continuous interface exists between the two fluids, e.g., an interface between two fluids completely filling their respect segments of a pipeline.

BRIEF DESCRIPTION OF THE DRAWINGS

The features and advantages of the invention described above, as well as others, will be more clearly understood with reference to the drawings, in which.

DETAILED DESCRIPTION OF THE PREFERRED EMBODIMENTS

Figure 1:
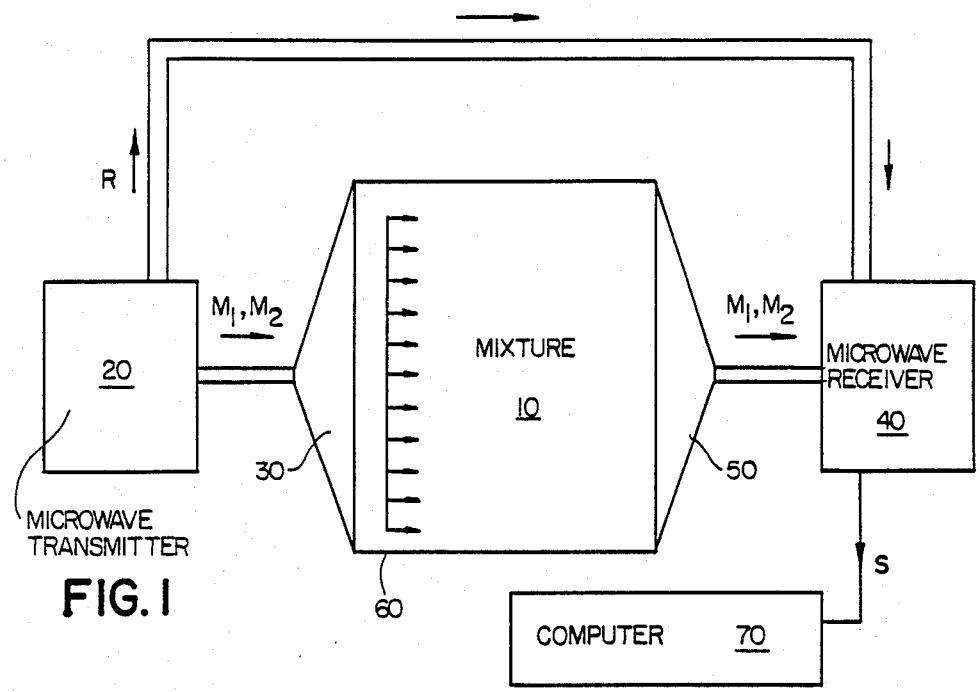
FIG. 1 is a partially schematic block diagram of a first exemplary embodiment of a fluid content measurement device according to the invention.

FIG. 1 is a partially schematic end-on view of an arrangement for measuring the volume fraction of a first fluid in a mixture (as defined above) of that fluid with another fluid, such as an oil-water mixture, according to the present invention. To make the discussion concrete, the arrangement will be described as it would be used in the continuous measurement of crude oil/water mixture flowing through a pipe, with flow being transverse to the plane of the figure. It will be understood, however, that the usefulness and scope of the device is not limited to this specific application.

The volume of oil-water mixture the water content of which is instantaneously being measured in FIG. 1 is designated by numeral 10. On one side of volume 10, the left side in FIG. 1, is first means for generating first and second microwave beams $M_1$ and $M_2$ comprising a microwave transmitter 20 and a transmit horn 30. Arranged across the volume from the first means, on the right-hand side in FIG. 1, is second means for receiving microwave beams $M_1$ and $M_2$ after they have been attenuated at least in part by water in the oil-water mixture 10. These means comprise a microwave receiver 40 and a receive horn 50. Beams $M_1$ and $M_2$ each have a wavefront parallel to line 60. These wavefronts propagate transverse to the flow of the oil-water mixture 10 and are received by receive horn 50. First and second microwave beams $M_1$ and $M_2$ as attenuated in the oil-water mixture 10 are preferably combined with a reference signal R also originating in microwave transmitter 20. Microwave receiver 40 then generates a signal S indicative of the degree of attenuation of beam $M_1$ and beam $M_2$ as compared to reference signal R. Signal S is fed to a computer 70 where it is processed to provide an on-line measurement of the volume fraction of water in oil-water mixture 10.

As mentioned above, there is a reference signal either passed from the generator to the receiver or otherwise provided to the receiver to provide a reference level of the transmitted power. The receiver then measures the received power, from which it is possible to calculate the power absorbed by the mixture in the pipe in a fashion which will now be described.

In an embodiment in which more than one frequency is used, the microwave absorption will be measured at each frequency propagated. For any given frequency, the average absorption of the fluid is:

$$\tilde{\alpha}_\nu = \frac{1}{B} \ln \frac{P_{T\nu}}{P_{R\nu}}$$

where
$\tilde{A}_\nu$ = average absorption at frequency $\nu$;
B = the distance through the fluid;
$P_{r\nu}$ = received power corrected for insertion loss, resonance effects, and other distortions; and
$P_{t\nu}$ = transmitted power.

The water content can be measured by measuring this value at more than one frequency, and taking advantage of the high absorption of water at about 23 GHz, the so-called "water absorption line." For example, if three measurements are made, one may be made at the water absorption line frequency and the other measurements can be made at frequencies differing from this frequency by the same amount. The results can then be combined algebraically to derive the volume fraction of water.

For example, let the frequency of the water absorption line be denoted by $\nu_1$, and the other two frequencies by $\nu_1 \pm \Delta \nu$. Assuming the oil absorption at frequency $\nu$, varies linearly with frequency in the form $$A_{o\nu} = A_o + A_o^1(\nu - \nu_1)$$

it can be shown that the volume fraction of water can be derived from these three absorption frequency measurements using the following formula:

$$V_W = \frac{2\tilde{\alpha}_{\nu 1} - \tilde{\alpha}_{\nu 2} - \tilde{\alpha}_{\nu 3}}{2\alpha_{w\nu 1} - \alpha_{w\nu 2} - \alpha_{w\nu 3}}$$

where
Vw = the volume fraction of water;
$\tilde{A}_{\nu 1}$ = average absorption at frequency $\nu_1$;
$\tilde{A}_{\nu 2}$ = average absorption at frequency $\nu_2$;
$\tilde{A}_{\nu 3}$ = average absorption at frequency $\nu_3$;
$A_{w\nu 1}$ = absorption of water in droplet form at frequency $\nu_1$;
$A_{w\nu 2}$ = absorption of water in droplet form at frequency $\nu_2$ and
$A_{w\nu 3}$ = absorption of water in droplet form at frequency $\nu_3$.

The advantages of this technique derive from the realization that variations in the absorption of oil will not affect the accuracy of the measurement as long as the variation is smooth. Additional measurements at additional frequencies will provide a more accurate value for water content. In the embodiments described above, the computations can be controlled by a small microcomputer, which calculates and reads out the results instantaneously. The computer can also be easily programmed to integrate the water volume to compute the total water volume passing through the pipe in a given time interval.

The above discussion assumes that the water is dispersed throughout the mixture in the form of small droplets. Where it is contemplated that water will occur not only in droplet form but also in the form of large globules, a different phenomenon may become dominant. This phenomenon will be referred to as "shadowing." The microwave energy impinging on such a globule of water is absorbed completely in the first fraction of a centimeter, so that the rest of the globule is ineffective in absorbing microwave energy. Very large droplets or globules, measuring more than a centimeter across, normally settle up in very quickly in storage tanks and do not comprise much of the water on-loaded to a tanker. In oil refineries, however, such slugs of water sometimes measuring a foot or more across can occur in refinery pipes and can cause serious damage to processing equipment.

Figure 2:
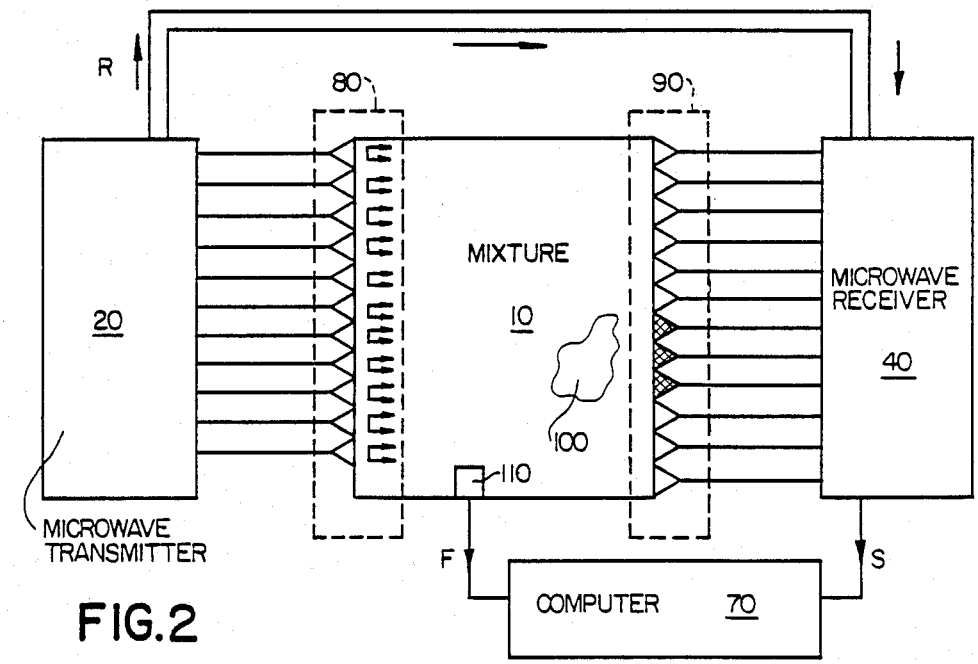
FIG. 2 is a partially schematic block diagram of a fluid distribution measurement device according to a second embodiment of the present invention.

The arrangement of FIG. 2 is intended to cope with these conditions. In FIG. 2, elements and signals have been assigned the designations used to identify their counterparts in FIG. 1. As can be seen, the apparatus in FIG. 2 also includes a microwave transmitter 20 and a microwave receive 40 as well as a computer 70. Transmit horn 30 has, however, been replaced with a linear array 80 of transmit horns. Similarly, receive horn 50 has been replaced by a linear array 90 of receive horns. This arrangement is advantageous in that it can detect the presence of large globules of water, represented in FIG. 2 by irregularly shaped blot 100. Water globule 100, assuming it is more than a few centimeters thick in the direction of propagation, will completely absorb any microwave radiation which impinges upon it. Thus, in the embodiment of FIG. 2, the receive horns in linear array 90 "behind" the globule (those which have been cross-hatched in FIG. 2) will be in the "shadow" of globule 100. By determining which of the receive horns in linear array 90 receive microwave radiation, the presence and extent of the water globule 100 can be determined and measured.

Figure 3:
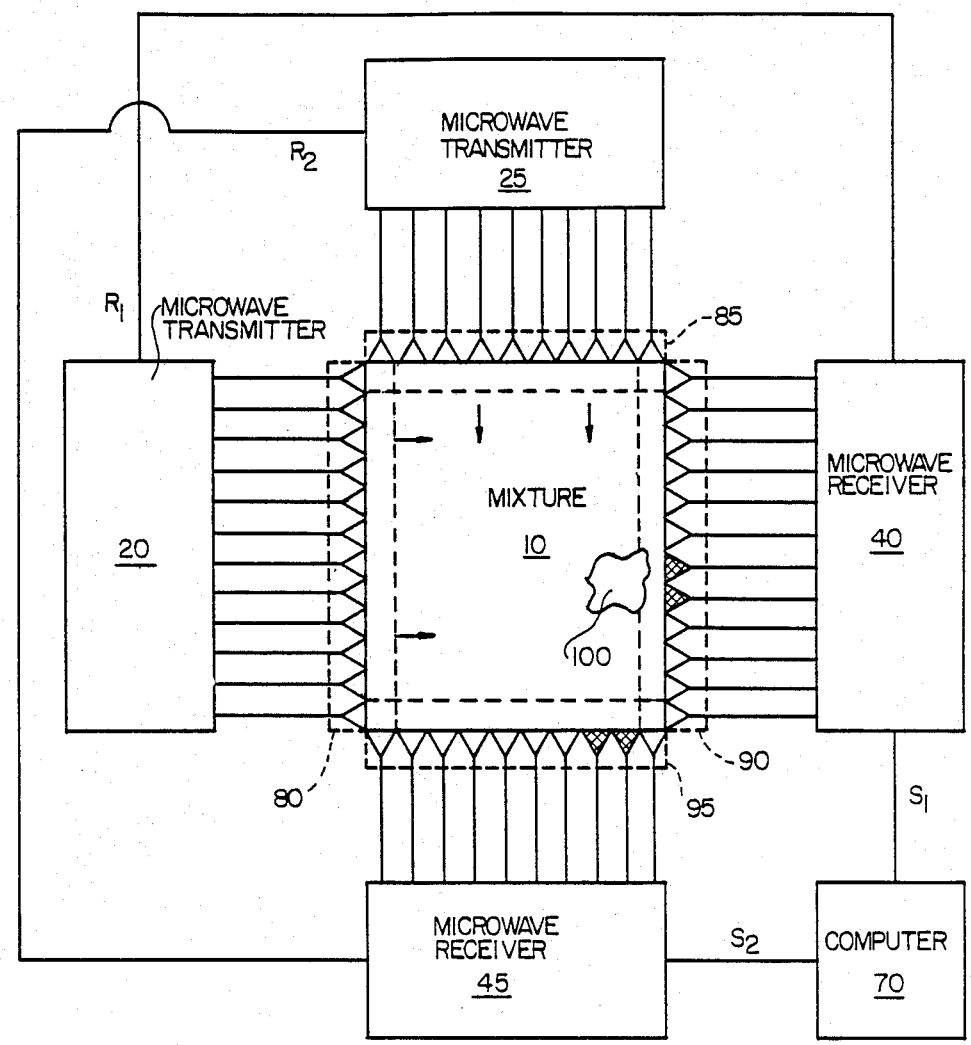
FIG. 3 is a partially schematic block diagram of a fluid distribution measurement device according to a third embodiment of the present invention.

Thus, in the embodiment of FIG. 2, each receiver acts as a sensor and measures absorption along one path through the volume. When a large globule of water crosses some of these paths the measured absorption of those paths will increase many tens of decibels. The dimension of the blob in the direction of the array is obtained from the number of sensors which detect this absorption, i.e., the number of sensors which are in the "shadow." The amount of absorption provides an indicator of the blob thickness in the beam direction. The length of time the absorption persists multiplied by flow speed in the pipe (measured by flow meter 110 in FIG. 2) provides an approximate measure of the third dimension of the blob. The volume of the blob can be calculated by a small microcomputer attached to the output. This shadowing technique may be made more accurate by using multiple sensors in both the horizontal and vertical axes of the cross plane of the pipe. This is shown in FIG. 3. In the embodiment of FIG. 3, an additional microwave transmitter 25 and an additional microwave receiver 45, with associated horn arrays 85 and 95, respectively, have been added. These additional components obtain the projection or shadow of water globule 100 in a direction perpendicular to the projection obtained by microwave transmitter 20 and microwave receiver 40. The details of adaptation to this two-dimensional system are straightforward and will be apparent to one having ordinary skill in the art.

Figure 4:
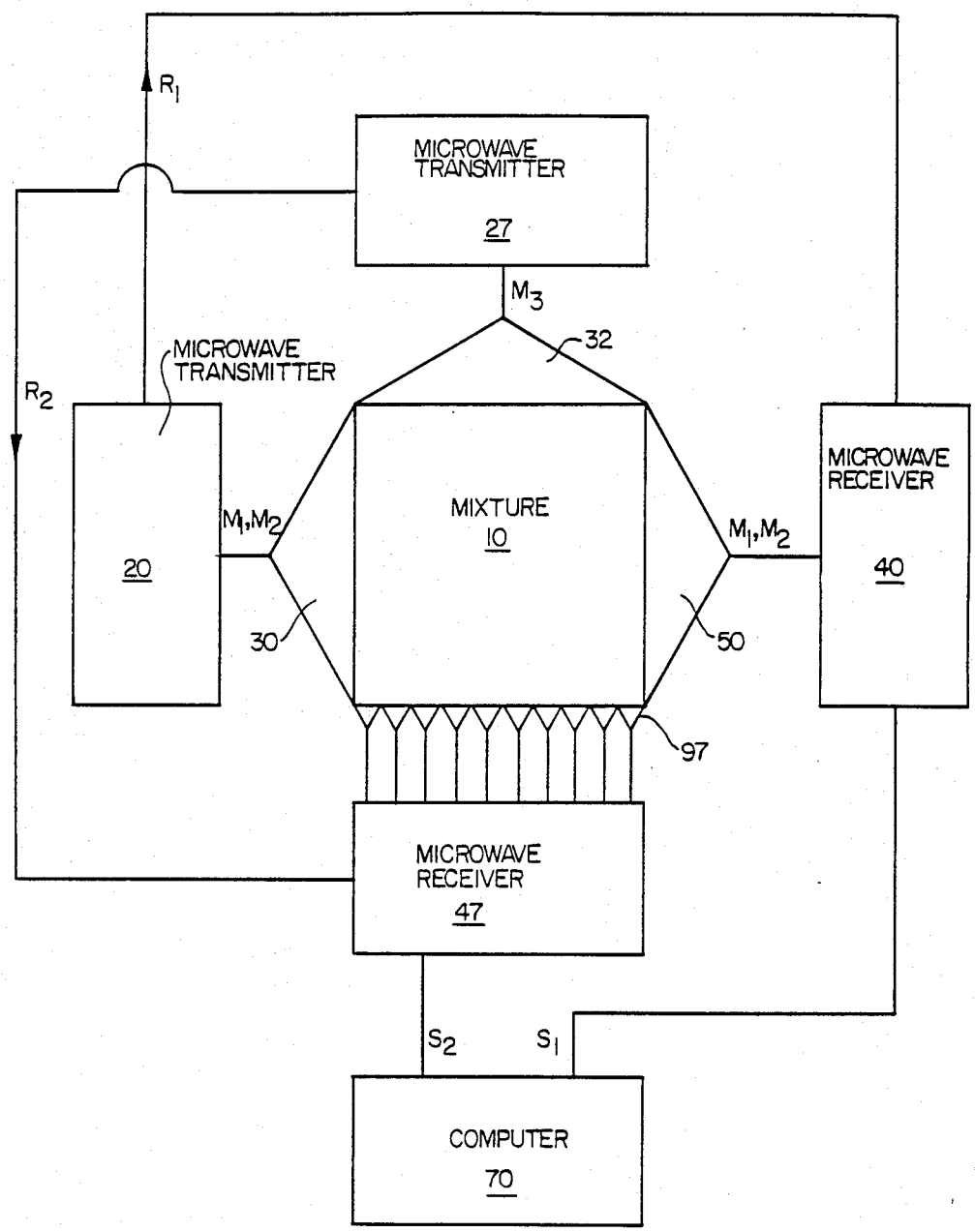
FIG. 4 is a partially schematic block diagram of a fluid content/distribution measurement device according to a fourth embodiment of the present invention.

The embodiment shown in FIG. 4 has both a broad-beam transmitter 20 transmitting two beams $M_1$ and $M_2$ as well as a linear array 97 of receive horns receiving a broad beam transmitted by transmitter 27 through antenna 32. The combination of components 20, 30, 50, 40 defines an apparatus such as that described in connection with FIG. 1 which provides data on the volume fraction of water in mixture 10. The combination of components 27, 32, 97, and 70 defines an apparatus giving information on the existence and location of large globules of water. The embodiment of FIG. 4 thus provides comprehensive data on the amount and distribution of water in mixture 10. It will be apparent to one having ordinary skill that the two combinations can be arranged so that their beams are parallel rather than transverse as shown in FIG. 4.

The above discloses a first system using two broad waves of different frequencies. It has also been mentioned above that these waves may be differentiated by timing and that measurement at additional frequencies will provide a more accurate value for water content. Combining these principles leads to an embodiment in which a succession of broad beams with incrementally or continuously increasing frequencies are passed through the volume under analysis. Conceptualized another way, a single beam's frequency can be swept or "chirped" continuously or in steps over a wide range of frequencies from below 10 GHz to over 20 GHz.

The chirp rate would be would be determined by the flow rate in the pipe, the width of the microwave beam, and by processing requirements. By using a wide range of microwave frequencies, the non-linear absorption which occurs in large globules or "slugs" of water, as discussed above, can be accounted for, and the water volume computed accurately even if there are many large globules of water or an irregular spectrum of sizes of water droplets suspended in the fluid.

Figure 5:
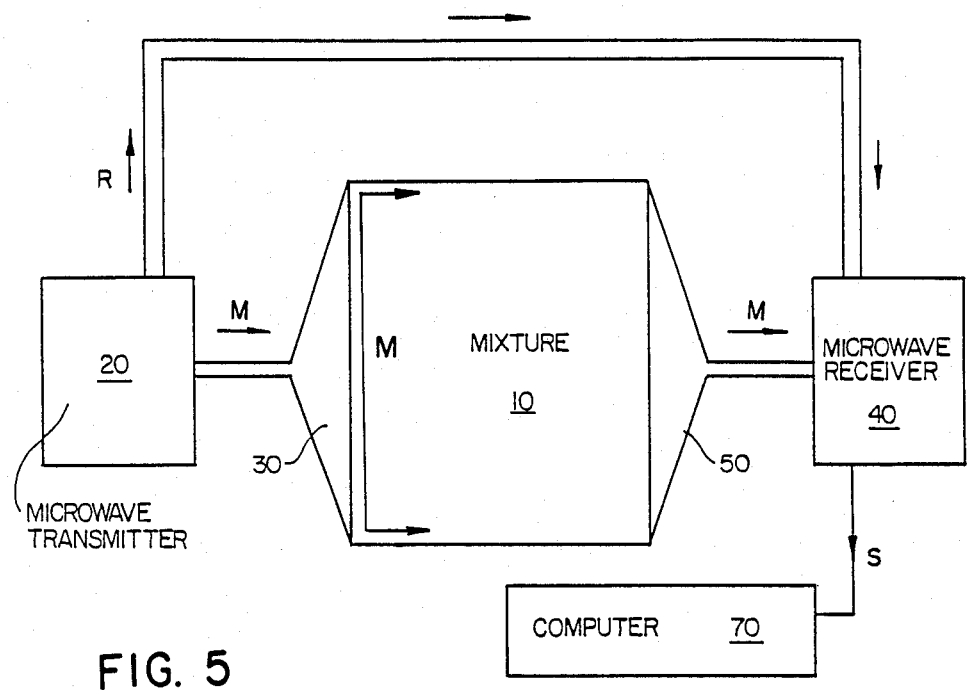
FIG. 5 is a partially schematic block diagram of a fluid content/distribution measurement device according to a fifth embodiment of the present invention.

One advantage of this technique is that a device embodying it can be constructed with simple and inexpensive components as shown in FIG. 5. The processing algorithm, which is described below, can be implemented on a microcomputer programmed to compute instantaneous and total integrated water content in the fluid which passes through the pipe.

As was the case in the other embodiments, when the crude oil or other material is flowing in the pipe, the instantaneous water content is computed by an on-line numerical processor, and is combined with information on flow rate in the pipe to compute the total volume of water carried through the pipe during some time interval. The flow rate in the pipe can be measured by a variety of conventional, well known, methods. One method is to place an orifice constriction downstream of the microwave device, and measure the pressure drop in the fluid upstream and downstream of the orifice, using simple pressure sensors. A second, more sophisticated method of measuring fluid flow velocity would utilize acoustic waves transmitted across the pipe at an angle, and measuring the travel time and doppler shift of the waves to compute average flow velocity in the pipe. Using one of these, or some other conventional technique, the flow rate can be measured. It is the purpose of the devices described above to measure the instantaneous fractional water volume of the fluid, and to combine this with the flow rate measurement to compute the total integrated water volume passing the measuring device.

The absorption of microwave energy by a volume of water or some other absorber can be described by a simple exponential law:

$$(1/E)\, dE/dx = -\gamma(\omega) \tag{2}$$

where E is the energy in the microwave beam, and the energy is propagating in the x direction. $\gamma(\omega)$ is a frequency dependent absorption parameter, which is equivalent to the inverse of the skin depth in the material. For a microwave signal of initial energy $E_o$, the beam intensity as a function of distance x is well known to be:

$$E = E_o\, e^{-\gamma(\omega)x} \tag{3}$$

Now suppose the beam passes through a medium, such as crude oil, in which microwave absorption is very low. However, there are water droplets of various sizes suspended in the oil, and these absorb the radiation strongly. For simplicity in the calculation, assume the shape of each water droplet is rectangular. The direction across the pipe in the beam direction will be x, the vertical direction across the pipe will be y, and the axis down the pipe will be z. It will be assumed there are many droplets in the beam of different sizes, so that the number of droplets having a specific set of dimensions will be denoted by $n_i$. Then denote the x dimension of a droplets by $\tau_1$, the y dimension by $h_i$, and the z dimension by $l_1$. The cross sectional area of the microwave beam is denoted by A.

The microwave absorption caused by the droplets and globules of various sizes can be added, by summing over the spectrum of droplets sizes, given by $n_i$. Then the microwave energy $E_h$ received by the microwave receiver can be related to the emitted microwave energy $E_o$ by $$E_h = E_o\,(1 - \Sigma n_i h_i l_i (1 - e^{-\tau_i \gamma(\omega)})/A) \tag{4}$$

Here, the sum is over all of the droplets in the beam, and this can be subdivided into droplets of various sizes, such that the thickness of the droplets in the x direction is the same for all droplets of the ith type.

The variation of received microwave power with a small change in microwave frequency can be calculated by differentiating Equation (4) with respect to frequency, resulting in:

$$dE_h/d\omega = -E_o/A\, \Sigma n_i h_i l_i \tau_i\, e^{-\tau_i \gamma(\omega)} \cdot \frac{\partial \gamma(\omega)}{\partial \omega} \tag{5}$$

and it will be noted that the product $n_i h_i l_i \tau_i = V_i$ the total volume of all of the water droplets having the x dimension of $\tau_i$. Then (5) can be rewritten:

$$dE_h/d\omega = -E_o/A \Sigma V_i\, e^{-\tau_i \gamma(\omega)} \frac{\partial \gamma(\omega)}{\partial \omega} \qquad (6)$$

This sum can be converted into an integral by converting the discrete parameter $V_i$ into a continuous spectral parameter $\nu(\tau)$. Since the water droplets were grouped according to those having the same x-dimension, the independent parameter in the continuous formulation is the x-dimension, or $\tau$. Then Equation (6) can be rewritten:

$$dE_h(\omega)/d\omega = -E_o/A \int \nu(\tau)\, e^{-\tau \gamma(\omega)} \frac{\partial \gamma(\omega)}{\partial \omega} d\tau \qquad (7)$$

Now define a new function $\phi(\omega)$ by:

$$\phi(\omega) = -\left( dE_h(\omega)/d\omega \left( \frac{\partial \gamma(\omega)}{\partial \omega} \right)^{-1} \right) A/E_o. \qquad (8)$$

Then Equation (7) may be written in the simpler form:

$$\phi(\omega) = \int \nu(\tau) e^{-\tau \gamma(\omega)} d\tau \qquad (9)$$

In this form it is clear the new function $\phi(\omega)$ is just the Laplace transform of the volume spectral function $\nu(\tau)$. The quantity of interest for the oil-water monitor is the integral of the volume spectral function $\nu(\tau)$ over $\tau$. This is the total water volume Q in the beam, and is given by:

$$Q = \int \nu(\tau) d\tau \qquad (10)$$

The water volume Q is the parameter of interest for the oil-water monitor. That parameter can be computed from Equation (9) by using the inverse Laplace transform to invert Equation (9) to solve for $\nu(\tau)$, then integrating this function over $\tau$ to obtain the total water volume in the beam. The Laplace transform can be converted into the Fourier transform by a simple change of variables, so the transformations described below can be converted to equivalent Fourier transforms, which are identical from the mathematical viewpoint. However, the Laplace transform is more closely related to the form of the equations, and so is used here for the purposes of explanation.

As is well known, if the Laplace transform is specified as in Equation (9), then the transform can be inverted to obtain $\nu(\tau)$ See, for example, Morse et al., *Methods of Theoretical Physics* at p. 1579. The function $\nu(\tau)$ is given by $$\nu(\tau) = \qquad (11)$$

$$\frac{1}{2\pi i} \int_{i\omega - \epsilon}^{i\omega + \epsilon} \left( - \frac{\partial E_h(\gamma)}{\partial \gamma} \right) \frac{A}{E_o} e^{\gamma t} d\gamma;\ \epsilon > \epsilon_o$$

Similarly, the total volume Q, as defined in Equation (10), can be related to $\nu(\tau)$ by:

$$Q = \int \nu(\tau) d\tau = \frac{1}{2\pi i} \int_{i\omega - \epsilon}^{i\omega + \epsilon} \phi(\gamma) \frac{1}{\gamma} e^{\gamma t} d\gamma;\ \epsilon > \epsilon_o \qquad (12)$$

and, using Equation (8), this can be expressed in terms of the measured quantities:

$$\text{Volume} = Q = \qquad (13)$$

$$\frac{1}{2\pi i} \int_{-i\omega + \epsilon}^{i\omega + \epsilon} \frac{1}{\gamma} \left( \frac{\partial E_h}{\partial \omega} \right) e^{\gamma t} d\omega;\ \epsilon > \epsilon_o$$

In this expression, the volume of water Q in the microwave beam is computed using the received microwave power $E_h$ and the emitted microwave power $E_o$, both of which may be functions of microwave frequency $\omega$. The expression also requires the area A of the microwave beam, and the function $\gamma(\omega)$, which describes the absorption rate of microwave energy in water as a function of frequency. This is a well-known relationship, and if it were not known it could be measured easily using this device. The above mathematical analysis does not depend on a specific functional form for $\gamma(\omega)$.

In practice, the microwave energy absorbed by the receiver will depend on other factors besides the water volume in the beam. The most important of these other factors will be resonances which occur at certain frequencies. These resonances depend on the dimensions of the walls of the pipe having a given ratio to the wavelength of the microwave radiation. These affect the coupling of the microwave transmitter and receivers. This will cause transmission of the microwaves across the pipe to have a varying efficiency less than unity for many microwave frequencies, even if there is no absorbing material in the pipe. However, this frequency dependent function can be measured by computing the received microwave power as a function of frequency when there is no absorbing material in the pipe. The function $\gamma(\omega)$ can be corrected empirically based on these measurements as part of the calibration of the apparatus. Since the function $\gamma(\omega)$ will be specified by the computer software utilized by the processing computer, the function $\gamma(\omega)$ can be easily modified to account for any systematic variation in coupling efficiency with frequency which may occur.

Figure 6:
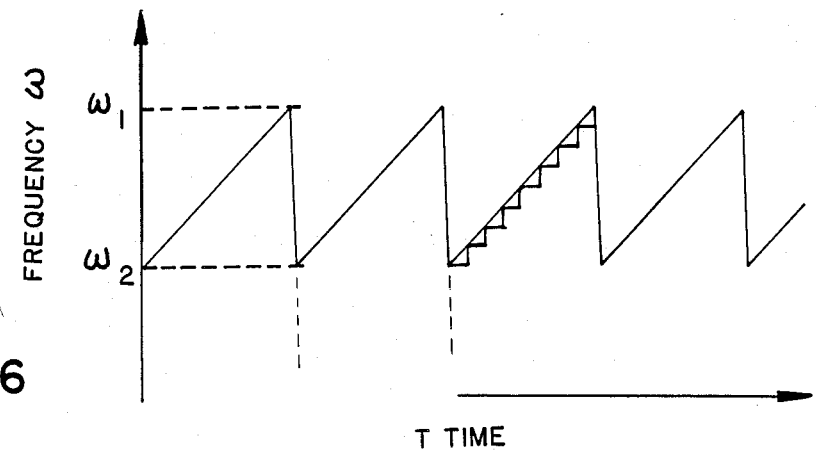
FIG. 6 is a graphical representation of a desirable variation of frequency with respect to time in a device as shown i FIG. 5.

The variation of frequency versus time which is assumed for this device may be described more explicitly mathematically, with the aid of FIG. 6. Let w(t) be a function which describes the frequency of the microwave radiation versus time during one chirp, where w is the frequency, and assume the total time for one chirp is T. Define w(t)=0 if t<0 or t>T. Now assume the elapsed time between the beginning of successive chirps is M, where $M \geq T$. (In the situation shown in FIG. 6, M=T) Then the frequency of the microwave transmitter as a function of time can be described by $$\omega(t) = \sum_{k=-\infty}^{k=\infty} w(t - kM) \qquad (14)$$

For a "linear" chirp, w(t) would be given as the product of t and a constant, the constant corresponding to the slope of the slanted portions of the waveform in FIG. 6.

There are several apparatus designs which can be implemented which can utilize the principle of the Inverse Laplace transform to compute the water volume. In each case, the device depends upon Equation (13), but it may be applied in several different embodiments.

In the first embodiment, the transmitter would be set up to maintain constant microwave power as it varies its frequency over the range from the minimum frequency $\omega_1$ to the upper frequency $\omega_2$. Then the function $\gamma(\omega)$, which embodies the damping rate of microwaves in water, as well as possible impedance mismatch or coupling factors, is implemented entirely in the software of the microcomputer which analyzes the measured power. The frequency derivative $dE_h/d\omega$ can be computed by comparing the received power levels at two nearby times, for which the frequency will be different because of the chirp. If the chirp is linear with time, then the frequency difference will be simply proportional to time difference within the chirp period.

In a second embodiment, the transmitter would be set up to vary its power with frequency according to $e^{\gamma(\omega)}$. The frequency is varied linearly with time. The receiver employs a time delay circuit and a subtractor, or differential amplifier, which has the effect of computing the derivative $dE_h/d\omega$ by an analog technique. Then the receiver need only to integrate and time average this signal to generate a signal proportional to the water content in the beam. This is an analog technique which requires minimal digital processing to compute the water volume.

In a third embodiment, two duplicate embodiments of the device are installed across the pipe, one having a beam in the horizontal, or x direction, and the second having a beam in the vertical, or y direction. The computed water volumes measured by the two systems can be compared by the computer to improve the accuracy of the measurement.

As described above, the microwave transmission system has three facets. The first uses at least two broad and coincident microwave beams of different frequencies. The second uses multiple narrow beams. The third uses a single broad, "chirped" beam. The broad beams measure the average water content in the pipe, so that the device using them is most accurate when the water is dispersed in fine droplets, i.e., where the droplets are on the order of half a centimeter or so. The narrow beam system computes a microwave absorption along each of many paths. Misidentification of the broad beams as the spatially-differentiated narrow beams is avoided by assigning frequencies to the broad beams which are different from frequencies assigned to the narrow beams. Misidentification can also be avoided by pulsing the broad and narrow beams out of phase with each other. The narrow beams may be differentiated by focusing antennae.

The embodiment in FIG. 1 would probably prove most useful in tanker on-loading monitors, while detection systems using multiple beams such as those of FIGS. 2 and 3 would have primary application in petroleum refineries, where large water globules could cause significant damage.

A device such as that shown in FIG. 4 would be flexible enough to measure water and air content in oil pipelines in a variety of applications in which it is not possible to do so now. For example, it is contemplated that the present invention will be very useful in the measurement and detection of multiphase flow in pipelines. Such a situation commonly occurs in pipelines in which water, oil, air, and/or other fluids occur in globules or strata. When this occurs, presently available monitors are not capable of measuring the fluid properties correctly. A device constructed according to the present invention would not have this disadvantage. Other applications might include use in nuclear power plants or in other pressure steam systems in which two phase flow occurs involving steam and condensed water.

A device according to FIG. 5 would be used in those situations requiring an extremely accurate measurement of water content/distribution. For example, during in tanker on-loading, real-time measurement of the oil, water, and air content of the oil could be made while the oil is being loaded into the tanker. This would eliminate any need for settling time of the water and eliminate legal disputes over excess water content in the oil. In refinery monitoring, real-time measurement of water content and refinery oil can be made, thus permitting warning or automatic shut-off of downstream processes which would otherwise be harmed by large slugs of water occurring the pipelines.

Another application would be as a furnace monitor. It is known that oil-burning furnaces can explode if a globule of water is injected while the furnace is burning. The cost of repair to such a system is many times the cost of oil monitor warning system according to the present invention.

An additional application would be monitoring of interfaces between different fluids in pipelines. Transcontinental pipelines transmit a variety of fluids in the same pipeline by loading first one fluid and then another in a sequential manner. It is very important to be able, at a downstream pumping or switching station, to measure when these interfaces occur, and to determine over what distance mixing and contamination of the fluids has occurred.

The present invention has been described above in terms of several exemplary embodiments. These embodiments have been described merely for the sake of elucidating the concepts underlying the invention. The description of specific embodiments should not be construed as a representation that only those embodiments are within the scope of the invention. Conversely, the fact that a particular embodiment has not been described should not be construed as an indication that embodiment is not within the scope of the present invention. Instead, the invention should be regarded as being fully commensurate in scope with the following claims, properly construed in accordance with the dictates of the applicable patent laws.

What is claimed is:

1. Apparatus for measuring a total volume of a first fluid having a first frequency dependent microwave energy absorption characteristic $\gamma(\omega)$ within a predetermined frequency range in a mixture of said first fluid and a second fluid, said second fluid having a second microwave energy absorption characteristic lower than said first microwave energy absorption characteristic in said predetermined frequency range, said mixture comprising volumes of said first fluid of various sizes, said apparatus comprising:

first means, arranged on one side of a volume of said mixture, for generating a microwave beam having an initial energy $E_o$ and a frequency $\omega$ which varies within said predetermined range;

second means, arranged across said volume from said first means, for receiving said generated microwave beam after it has passed through the mixture, and for generating signals $E_h$ indicative of attenuation of the initial energy of said microwave beam in said mixture as said frequency varies; and third means, coupled to said second means and responsive to said signals $E_h$, for determining the total volume $V_i$ of said first fluid in said mixture by summing all of the various size volumes of said first fluid in accordance with their spatial dimension $\tau i$ in a direction parallel to the direction of propagation of the microwave beam.

2. An apparatus as claimed in claim 1 wherein said first means comprises a microwave transmitter and a transmit horn, the transmit horn being arranged adjacent said volume.

3. An apparatus as claimed in claim 1 wherein said second means comprises a microwave receiver and a receive horn, said receive horn being arranged adjacent said volume.

4. An apparatus as claimed in claim 1 wherein said frequency of said microwave beam sweeps a range of frequencies varying by at least a factor of two.

5. An apparatus as claimed in claim 1 wherein said third means comprises a microcomputer.

6. An apparatus as claimed in claim 1 where said first means maintains a constant energy microwave beam as said frequency varies with time, and wherein said determining means stores and uses the characteristics function $\gamma(\omega)$.

7. An apparatus as claimed in claim 1 wherein said third means further comprises fourth means, responsive to the first means, for measuring a variation of the initial energy and frequency $\omega$ of said microwave beam, said third means including means for comparing said variation with said received microwave beam at the second means to determine absorbed energy.

8. A method for measuring a total volume of a first fluid having a first frequency dependent microwave energy absorption characteristic $\gamma\omega$ within a predetermined frequency range in a mixture of said first fluid and a second fluid, said second fluid having a microwave energy absorption characteristic lower than that of said first fluid within said frequency range, said mixture comprising values of said first fluid in various sizes, said method comprising the steps of:

(a) generating a microwave beam having an initial energy $E_o$ and a frequency $\omega$ which varies within said predetermined range with time;

(b) transmitting said microwave beam through a volume of said mixture;

(c) receiving said microwave beam;

(d) determining attenuation of the initial energy of said first microwave beam as a function of frequency as it passes through said volume;

(e) producing signals $E_h$ indicative of said attenuation; and (f) determining the total volume $V_i$ of said first fluid by summing all volumes of the various sizes of the first fluid having the spatial dimension $\tau i$ in the direction of propagation of the microwave beam;

(g) dividing the volume $V_i$ by the area of said microwave beam.

9. A method as claimed in claim 8 wherein said step (a) comprises maintaining said beam at constant energy as said frequency varies with time, and wherein said step (f) comprises utilizing the absorption characteristic $\gamma(\omega)$.

10. A method as claimed in claim 8 wherein said step (a) further comprises measuring the initial energy $E_o$ of the generated beam as a function of frequency $\omega$, and wherein said determining is based at least in part on results of the energy measurement.

11. A method as claimed in claim 10 wherein said step (a) comprises sweeping said frequency over a range of frequencies varying by at least a factor of two.

12. A method as claimed in claim 11 wherein said sweeping is carried out continuously.

13. A method as claimed in claim 11 wherein said sweeping is carries out incrementally.

14. Apparatus for measuring a volume fraction of a first fluid in a mixture of said first fluid and a second fluid, one of said fluids having a microwave energy absorptivity greater than that of the other, said apparatus comprising:

first means, arranged on one side of a volume of said mixture, for generating a microwave beam having a frequency which varies with time;

second means, arranged across said volume from said first means, for receiving said generated microwave beam after it has passed through the mixture, and for generating signals indicative of attenuation of said microwave beam in said mixture as said frequency varies; and third means, electrically connected to said second means and responsive to said signals, for calculating said volume fraction of said first fluid in said mixture based on said signals;

wherein said first means varies its power with frequency according to exp $(\gamma(\omega))$, wherein $\gamma(\omega)$ is a function characteristic of absorption of microwave energy in said first fluid with respect to frequency.

15. Apparatus for measuring a volume fraction of a first fluid in a mixture of said first fluid and a second fluid, one of said fluids having a microwave energy absorbtivity greater than that of the other, said apparatus comprising:

first means, arranged on one side of a volume of said mixture, for generating a microwave beam having a frequency which varies with time;

second means, arranged across said volume from said first means, for receiving said generated microwave beam after it has passed through the mixture, and for generating signals indicative of attenuation of said microwave beam in said mixture as said frequency varies; and third means, electrically connected to said second means and responsive to said signals, for calculating said volume fraction of said first fluid in said mixture based on said signals:

wherein (a) said first means includes means for varying output power with frequency in accordance with a first function; and (b) said third means includes means for storing data indicative of said first function and for performing calculations based at least in part on said data such that with measurement of received power, absorption can be measured as a function of frequency.

16. A method for measuring the volume fraction of a first fluid in a mixture of said first fluid and a second fluid, one of said fluids having a microwave energy absorptivity greater than that of the other, said method comprising the steps of:

(a) generating a microwave beam having a frequency which varies with time;

(b) transmitting said microwave beam through a volume of said mixture;
(c) receiving said microwave beam;
(d) determining an attenuation of said first and microwave beam as a function of frequency;
(e) producing signals indicative of said attenuation; and
(f) calculating said volume fraction of said first fluid on the basis of said signals;
wherein said step (a) comprises varying the power of said microwave beam according to exp ($\gamma(\omega)$)), wherein $\gamma(\omega)$ describes said absorptivity of microwave energy of said first fluid as a function of time.

17. A method for measuring the volume fraction of a first fluid in a mixture of said first fluid and a second fluid, one of said fluids having a microwave energy absorptivity greater than that of the other, said method comprising the steps of:

(a) generating a microwave beam having a frequency which varies with time;
(b) transmitting said microwave beam through a volume of said mixture;
(c) receiving said microwave beam;
(d) determining an attenuation of said first and microwave beam as a function of frequency;
(e) producing signals indicative of said attenuation; and
(f) calculating said volume fraction of said first fluid on the basis of said signals;
wherein power of said microwave beam is caused to vary with frequency in a known and reproducible manner, and wherein said determining is based on the known and reproducible variation of microwave beam power, such that said attenuation is measured as a function of frequency.

* * * * *